(12) United States Patent
Friedmann et al.

(10) Patent No.: US 8,293,523 B2
(45) Date of Patent: Oct. 23, 2012

(54) AGITATOR FOR A FERMENTER, FERMENTER AND METHOD FOR OPERATING A FERMENTER

(75) Inventors: Johann Friedmann, Scheyern-Fernhag (DE); Christian Heck, Bissen (LU)

(73) Assignee: Agraferm Technologies AG, Pfaffenhofen/Ilm (DE)

( * ) Notice: Subject to any disclaimer, the term of this patent is extended or adjusted under 35 U.S.C. 154(b) by 1233 days.

(21) Appl. No.: 12/065,520

(22) PCT Filed: Aug. 30, 2006

(86) PCT No.: PCT/EP2006/008488
§ 371 (c)(1),
(2), (4) Date: Apr. 8, 2008

(87) PCT Pub. No.: WO2007/025739
PCT Pub. Date: Mar. 8, 2007

(65) Prior Publication Data
US 2008/0248519 A1    Oct. 9, 2008

(30) Foreign Application Priority Data
Sep. 2, 2005 (DE) .......................... 10 2005 041 798

(51) Int. Cl.
C12M 1/02      (2006.01)
C12M 1/107    (2006.01)
B01F 7/18      (2006.01)

(52) U.S. Cl. .................. 435/289.1; 435/300.1; 366/251; 366/331

(58) Field of Classification Search ............... 435/289.1, 435/300.1; 366/247, 251
See application file for complete search history.

(56) References Cited

U.S. PATENT DOCUMENTS 5,064,086 A * 11/1991 McEntee ........................ 220/253
5,568,985 A * 10/1996 Schutte .......................... 384/478
7,387,431 B2 * 6/2008 Blakley .......................... 366/331

FOREIGN PATENT DOCUMENTS

| DE | 19947340 A1 * | 5/2001 |
| DE | 202004004101 U1 | 7/2004 |
| DE | 202004012236 U1 | 11/2004 |
| EP | 1394246 A1 | 3/2004 |

OTHER PUBLICATIONS

Machine translation of DE20 2004 004101 (Jul. 29, 2004).*
Machine translation of DE 20 2004 012236 (Nov. 25, 2004).*
International Search Report for PCT/EP2006/008488 mailed Mar. 1, 2007, four pages.

* cited by examiner

*Primary Examiner* — William H Beisner
(74) *Attorney, Agent, or Firm* — Rankin, Hill & Clark LLP

(57) ABSTRACT

An agitator for a fermenter, a fermenter and method of operating a fermenter are provided. The agitator has an agitator shaft which stands roughly vertically in the fermenter. Because of this, the substrate in the fermenter is circulated in horizontal planes. This allows the formation of several layered decomposition zones. In addition, the agitator is preferably designed so that it may be removed upwards from the fermenter during continuing operation. This means that it is not necessary to empty the fermenter for maintenance work on the agitator.

17 Claims, 9 Drawing Sheets

AGITATOR FOR A FERMENTER, FERMENTER AND METHOD FOR OPERATING A FERMENTER

Figure 1:
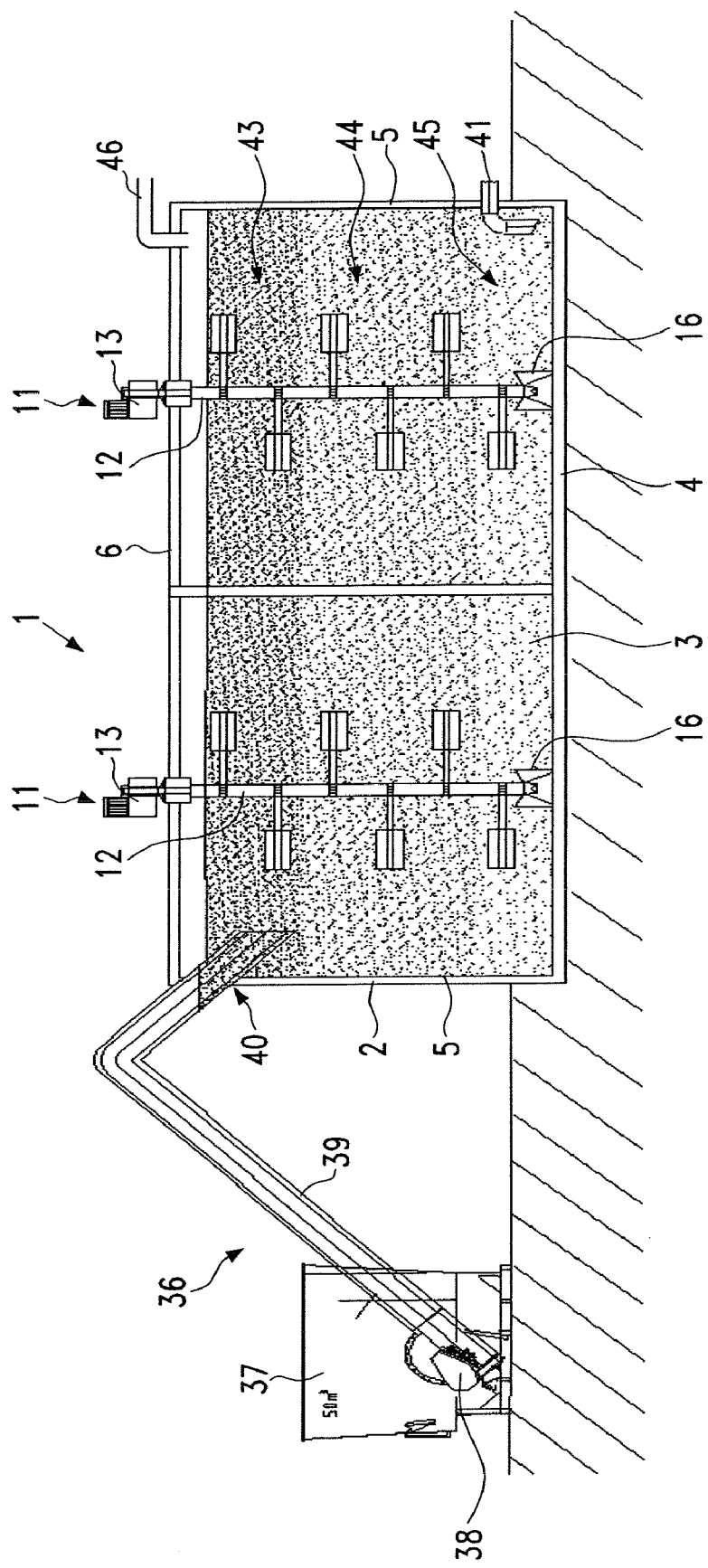

The present invention relates to an agitator for a fermenter, a fermenter and a method of operating a fermenter.

To produce biogas, fermenters are used as fermenting vessels, with the resulting biogas being burned in boilers or motors for power generation. As feed materials for the biogas production, in principle all kinds of biomass may be used which have as their main components carbohydrate, protein, fats and cellulose. The organic substances which may be used for biogas production are mostly residual products or by-products from various sectors and areas of activity. From agriculture for example, liquid and solid manure, residues from plant production, but also plants specially cultivated for this purpose, for example maize, are used. Plant residues from brewing and the vegetable processing industry may also be used, together with organic sludge and effluent from industrial processing. In addition it is also possible to use animal products or products of municipal waste disposal.

Biogas is a gas mixture resulting from the anaerobic, microbial decomposition of organic substances, with 50% to 70% comprised of the high-value energy carrier methane (CH4). Other constituents are 30% to 40% carbon dioxide (CO2), plus traces of hydrogen sulphide, nitrogen, hydrogen and carbon monoxide.

On account of its relatively high energy content, biogas may be utilised as energy carrier for heat and power generation. The average heating value of biogas is around 6,000 kcal/m3 (=25,000 kJ/m3). The heating value of one m3 therefore corresponds to around 0.6 l of heating oil.

The use of fermenters in biogas plants, with a typical volume for example of 150 m3 to 3,000 m3, is known. In individual cases the fermenters may also be much larger. For example a fermenter for a biogas plant with a volume of 8,000 m3 is known. The substrate is held in the fermenter for several days, with biogas being created by the activity of microorganisms. Through biochemical transformation, the biogas is desulphurised in the fermenter, which involves hydrogen sulphide being converted into sulphur when oxygen is supplied to the gas space of the fermenter. To avoid the formation of scum layers and settling layers the substrate is stirred, depending on its composition. This also facilitates the escape of the evolving gases. The fermented substrate is then removed to a final storage place, which should be sealed as far as possible, since residual biogas may escape.

The freshly produced biogas is then dried and cleaned with a safety filter. The remaining biomass after fermentation is suitable as biological fertiliser. With regard to the structure of a biogas plant, reference is made to German utility model patent DE 20 2005 012 340.

To date, horizontal fermenters have mainly been used for dry fermentation. Such horizontal fermenters are formed for example by a very long thin hollow body containing an agitator with a single shaft extending over the entire length of the fermenter. The length of such a fermenter may be for example up to 25 m. The ends of the agitator shaft of the agitator are mounted in the opposing walls of the fermenter body. An agitator shaft of this length is mechanically difficult to control, since considerable moments occur at the shaft. Consequently there are also fermenters with several agitator shafts, each running horizontally and at right-angles to the axial direction of the fermenter. Here the mechanical loading of the individual agitator shafts is significantly less, but each agitator shaft requires a separate drive mechanism, which in turn incurs considerable cost. In addition, the sealing of the supports of the shafts in the side walls of the fermenter is extremely problematic. This fermenter too forms an elongated passage into which the input materials are fed at one end and the fermented products are removed from the other end. Such a passage generally has a rectangular cross-section and is comprised of concrete segments. The production of a rectangular concrete passage is expensive.

Irrespective of the manner of construction of the fermenter, there is the problem with these known fermenters that, to replace an agitator, it is necessary to empty the fermenter, in order to gain access to the mounting points in the fermenter body. Since the agitators are subject to unavoidable wear, operation of the fermenter must be interrupted at regular intervals in order to service the agitators.

DE 20 2004 004 101 U1 discloses a fermenter for a biogas plant with an agitator device which has an upright agitator shaft. At its lower end this is in the form of a hollow shaft, so that it may be pushed over a guide tube mounted immovably in the fermenter. The agitator shaft is equipped with hinged agitator paddles, so that the agitator shaft may easily be removed vertically for servicing or repair.

Known from DE 20 2004 012 236 U1 is another agitator with a rotary shaft mounted at an angle. Integrated in the lower end of this rotary and agitator shaft is a bearing unit, so that for servicing or repair work the bearing together with the rotary shaft is removed from the fermenter.

DE 20 2004 005 331 U1 describes an agitator which may be removed through an opening in a side wall or roof of a fermenter vessel. This agitator has an elongated tube, the end of which is loosely inserted in a mating bearing. Mounted in the tube is a shaft which rotates agitator elements fitted to the outside of the tube.

Described in DE 44 19 782 A1 is a horizontal fermenter provided with a centrally supported agitator shaft. The shaft is divided in the centre, with the respective ends supported by a centre bearing.

DE 10 2004 027 077 A1 discloses another agitator for a fermenting vessel, which may be inserted into the vessel at an angle. With its free end the agitator rests on a mounting stand, relative to which it is pivotably mounted.

DE 20 2004 017 610 U1 describes a biogas plant with a fermenter, in which is provided an agitator with a horizontal shaft. In this embodiment, material for fermentation is fed in at the top, with an outlet for removal of the fermented material near the base.

DE 201 21 701 U1 describes an apparatus for the decomposition of organic substances. This has a reactor or fermenter in which organic substances are floated from an inlet to an outlet located at a distance from the former and substantially on the same horizontal level. This is intended to facilitate quasi-continuous process guidance, and breaking up of the organic substances may also be dispensed with.

DE 201 11 480 U1 shows a fermenter with an agitator which is rotated around a vertical agitator shaft. Located a short distance from the shaft are agitator means which keep the contents of the fermenter in motion. Let into the base at the edge of the fermenter is a sump into which the sediments forming at the base of the fermenter are guided. The sediments settling here are removed from the sump by means of a pipe.

DE 200 11 783 U1 discloses a fermenter of similar design, provided at its edge with a kind of sump, from which the sediments settling in the fermenter may be removed by means of a screw conveyor.

DE 102 24 665 A1 shows a fermenter in the form of a closed vessel in which the material to be fermented is fed in at the top, and removed the bottom. This fermenter is provided with agitator means capable of rotating around a vertical axis.

DE 31 38 452 A1 shows another fermenter with a cylindrical fermentation vessel with an inlet pipe in the upper part of the vessel and an outlet pipe diametrically opposite in the lower part of the vessel.

EP 1 394 246 A1 discloses an agitator device for a fermenter which has a cylindrical fermentation vessel. Mounted on the radial outside of each fermenting vessel are two agitator shafts which both swirl the contents around in their immediate vicinity and also circulate them around the whole of the vessel.

This fermenter may be provided in particular with an agitator module in which the two agitator shafts and the drive motor are integrated. The agitator module may be removed as a unit vertically from the fermenter for repair and maintenance work. At the base of the fermenter are receptacles to accommodate the ends of the agitator shafts.

EP 0 307 500 A1 describes a portable biogas generator with a tilted cylindrical container mounted on a vehicle. On one end wall the container has a filling nozzle, and on the cylindrical surface it has a discharge outlet.

DE 196 21 914 C1 shows another fermenter with a type of sump in the middle of the fermenter, from which settling layers may be removed by means of a screw drive. The invention is based on the problem of creating an agitator for a fermenter, a fermenter, and a method of operating a fermenter, which permit easier and more efficient operation of the fermenter.

The problem is solved by an agitator, a fermenter, a method with the features of the appended claims. Advantageous developments of the invention are set out in the relevant dependent claims.

The agitator according to the invention for a fermenter, in particular a fermenter for dry fermentation, comprises:
at least one vertical agitator shaft, to which is fitted one or more paddles,
a drive mechanism to rotate the agitator shaft, with the drive mechanism acting on the upper end section of the agitator shaft, and
a centring bearing for centring the lower end of the agitator shaft, wherein the centring bearing is designed to be releasable from the agitator shaft in such a way that the agitator shaft may be centred by pushing into the centring bearing and held in the latter solely by the force of gravity of the agitator shaft, and the centring bearing has an insertion funnel and is provided with a centring section, and
at the lower end section of the agitator shaft there is provided a stub shaft, mounted by means of a bearing so as to be rotatable relative to the rest of the agitator shaft, and the stub shaft has a coupling element which engages positively with some play in the centring section.

With this agitator it is possible to pull the agitator shaft upwards from the centring bearing during operation of the fermenter, and to remove it from the fermenter. The agitator shaft may then be serviced and reinserted in the centring bearing in the fermenter, or else replaced by another agitator shaft. There is no need to empty the fermenter for this purpose, so that the agitator shaft may be replaced much more quickly than is the case with conventional fermenters. If the fermenter has one or more additional agitator shafts, operation may still be continued.

The centring bearing has an insertion funnel which facilitates insertion of the agitator shaft into the centring bearing. The insertion funnel is mounted immovably in the fermenter, so that in principle it may be of any size desired. Insertion aids on agitator shafts are known. However, these have the disadvantage that, in the case of a fermenter filled with substrate, they must displace the substrate. In the case of the agitator according to the invention, only the relatively thin elongated agitator shaft with the paddles is moved through the substrate.

Also provided at the lower end section of the agitator shaft is a stub shaft which, by means of a bearing, is mounted so as to be rotatable relative to the rest of the agitator shaft. This bearing for rotating the shaft represents the most labour-intensive part of the agitator shaft. With the mounting of the bearing in the agitator shaft, the bearing may be removed from the fermenter and serviced together with the agitator shaft. Since the stub shaft is provided with a coupling element which engages positively with some play in a centring section of the centring bearing, the stub shaft is mounted non-rotatably in the fermenter, so that the agitator shaft is mounted in a defined manner by means of the bearing provided between the stub shaft and the remainder of the agitator shaft.

Preferably the centring bearing has in its lower section an opening from which material may be displaced when the agitator shaft is inserted into the centring bearing.

According to claim 9, the invention has an agitator in which the agitator shaft is equipped with several agitator paddles, which may be set at different angles relative to the vertical. This makes it possible to adjust to the viscosity of the substrate in the fermenter. In this connection it is also possible to provide several agitator paddles on the agitator shaft, with different angles of inclination, so that substrate layers of different viscosity may be subject to varying degrees of pressure.

If the agitator paddles are set mainly vertically, then they will mix the substrate only in the radial direction. By this means it is possible to react specifically to separate layers in the fermenter. If the agitator paddies are set at an angle to the vertical then, depending on the degree of inclination, the substrate will be mixed increasingly in the vertical direction. Adjustment of the inclination of the agitator paddles thus permits control of the substrate flows in the fermenter. The combination of a vertically aligned shaft and agitator paddles with adjustable angles of inclination allows a targeted approach to the substrate layer by layer.

The fermenter according to the invention comprises:
a housing with at least one baseplate and one or more side walls enclosing the baseplate,
an agitator according to the invention, for mixing the substrate in the fermenter, a feeding device for the feeding in of input materials, and
a discharge outlet, wherein the feeding device for feeding in the input materials is located in the top section of the fermenter and the discharge outlet is at the bottom section of the fermenter.

In the fermenter according to the invention the flow is therefore from top to bottom, which facilitates continuous operation, while three zones with material of different density may form in the fermenter. The topmost zone is the liquefaction zone, in which the introduced substrate is liquefied. The middle zone is the methanation zone in which the already liquefied and somewhat compacted material releases the major part of its methane. In the bottom zone, the discharge zone, is found the completely or almost completely decomposed substrate, which has the greatest density. Due to the through flow from top to bottom, the decomposition stages are hydraulically decoupled, which optimizes the gas yield.

In the preferred embodiment of the fermenter according to the invention, the agitator is provided with a vertically aligned agitator shaft. By this means, agitator paddles joined to the agitator shaft are each moved in a horizontal plane, and the substrate in the fermenter is mixed in horizontal planes. This encourages the formation of the decomposition zones described above.

The method according to the invention for operating a fermenter, in particular a fermenter for dry fermentation for biogas plants, is distinguished by the fact that input materials for the dry fermentation are fed in to the top section of the fermentation, and the fermented substrate is removed from the bottom section of the fermenter.

The through flow from top to bottom facilitates the zoning referred to above.

Preferably the substrate of the fermenter is mixed radially, which promotes the zone formation. For this it is also necessary for the mixing to take place slowly, for example with a speed of rotation of the agitator shaft(s) in the range of 0 to 20 rpm or up to a maximum of 60 rpm.

If the fermenter is operated with this zone formation, then the starting material fed in at the top is gradually converted into the product, at the same time sinking downwards in the fermenter. Such fermenters are also described as tube reactors or plug flow reactors. The facility to adjust the inclination of the agitator paddles, however, also permits a different mode of operation of the fermenter, in which the substrate is mixed vertically from top to bottom or from bottom to top.

Preferably the fermenter is operated with the zone formation described above, with however a certain inclination of the agitator paddles being set in the upper section, so that freshly introduced starting material is mixed more intensively with the substrate already in the fermenter.

Figure 2:
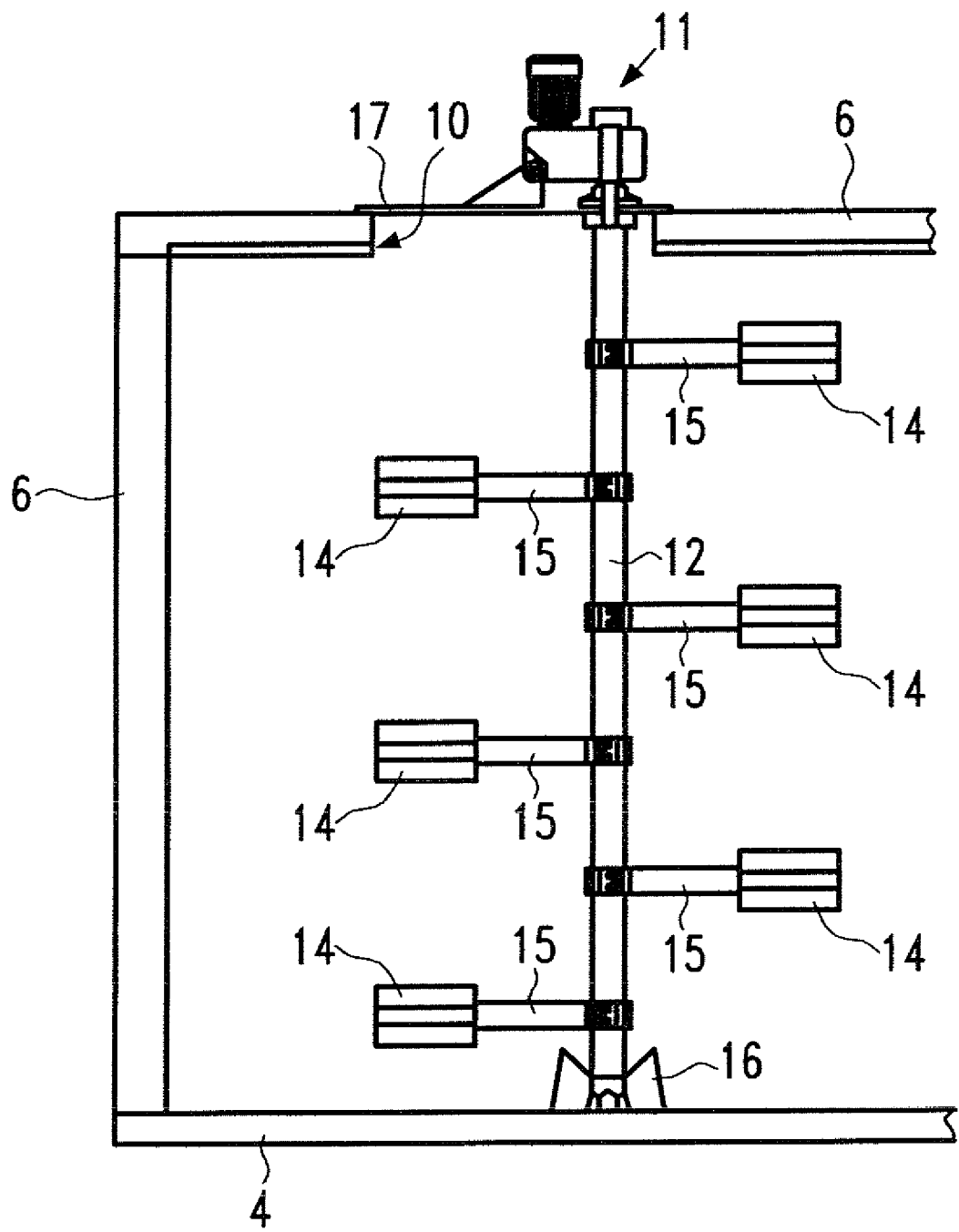
Figure 3:
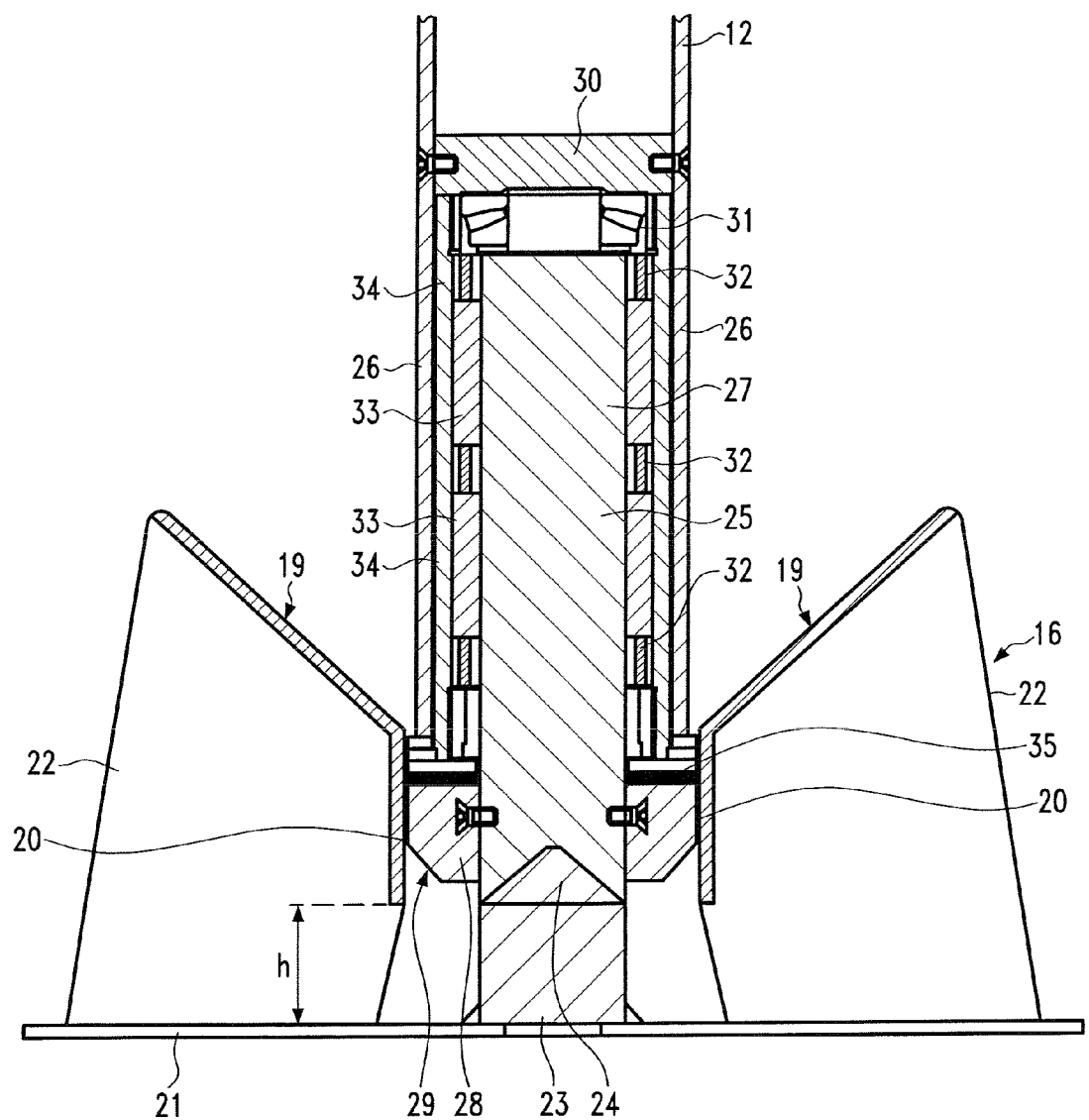
Figure 4:
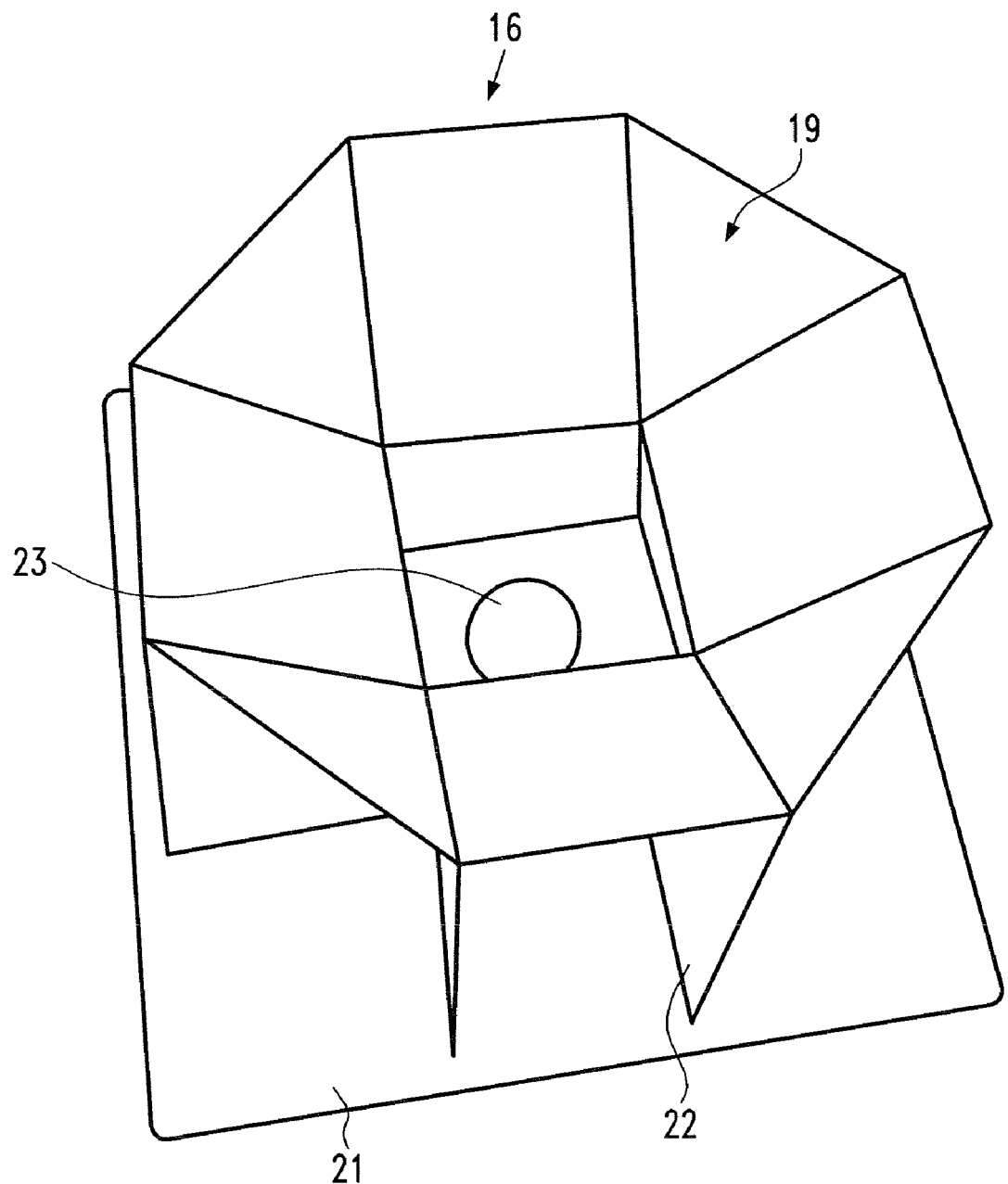
Figure 5:
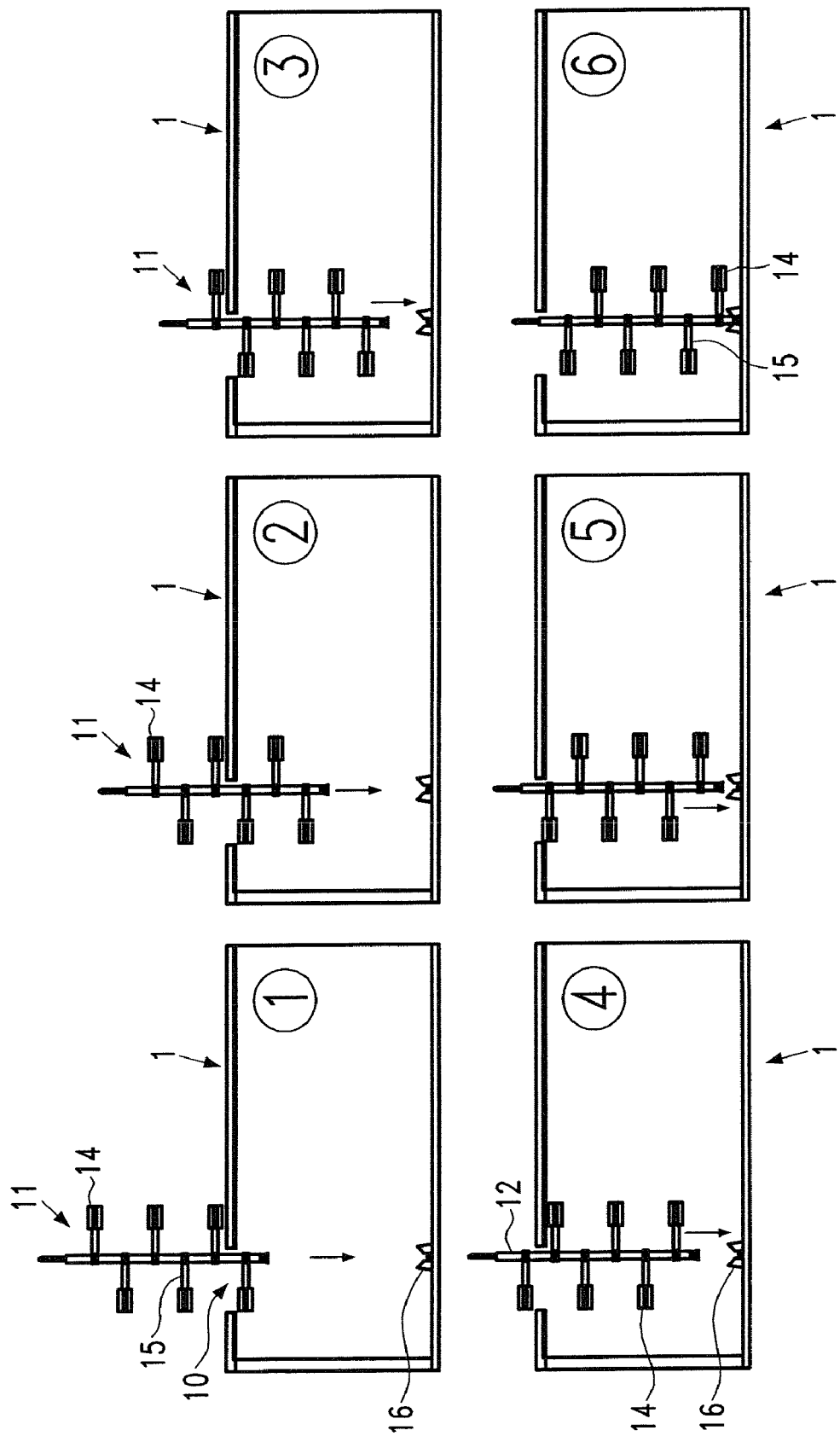
Figure 6:
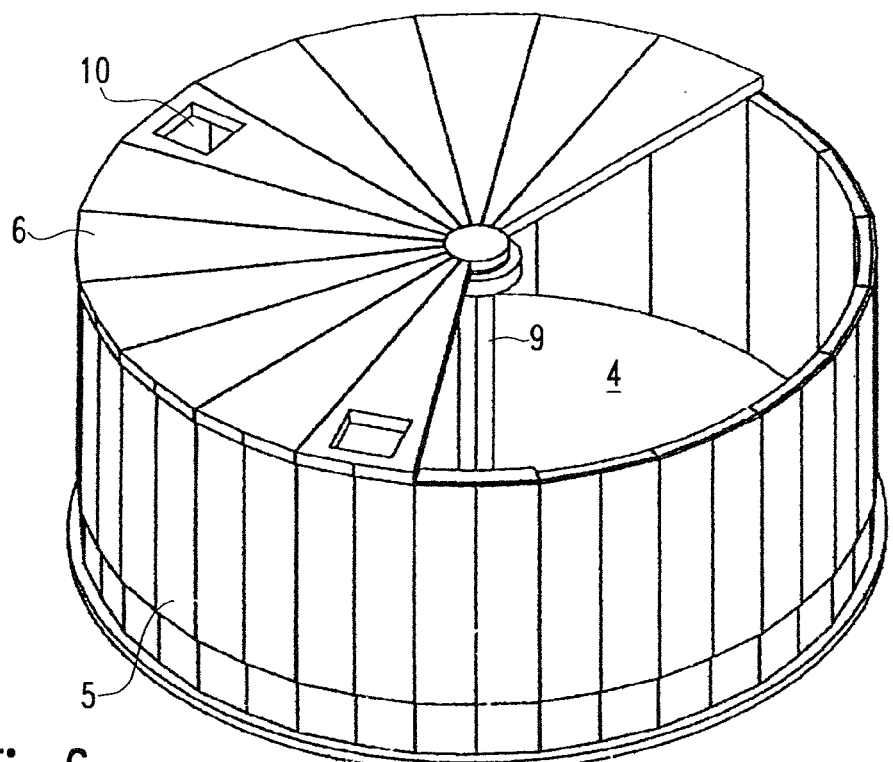
Figure 7:
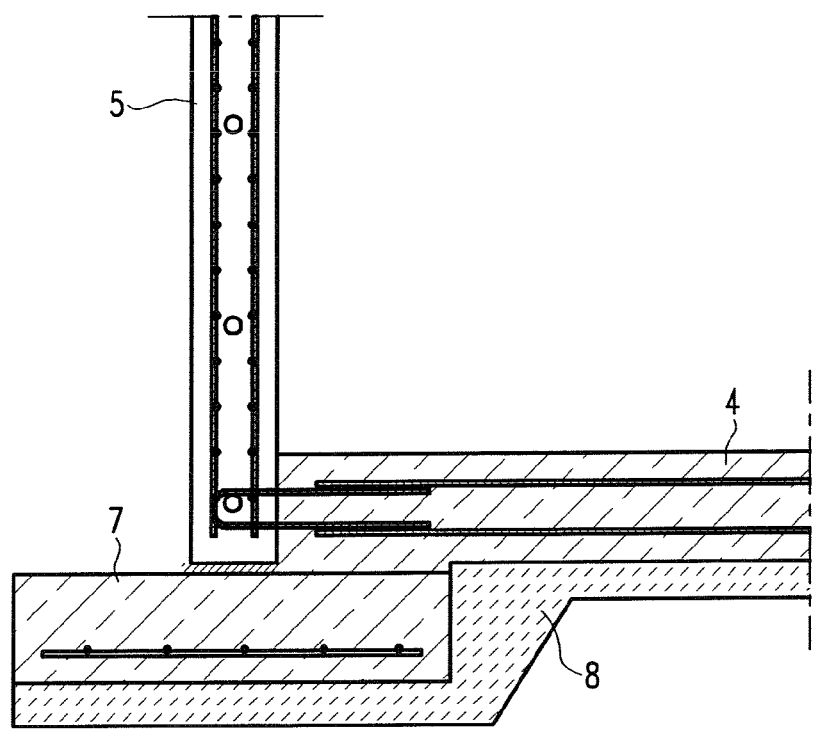
Figure 8:
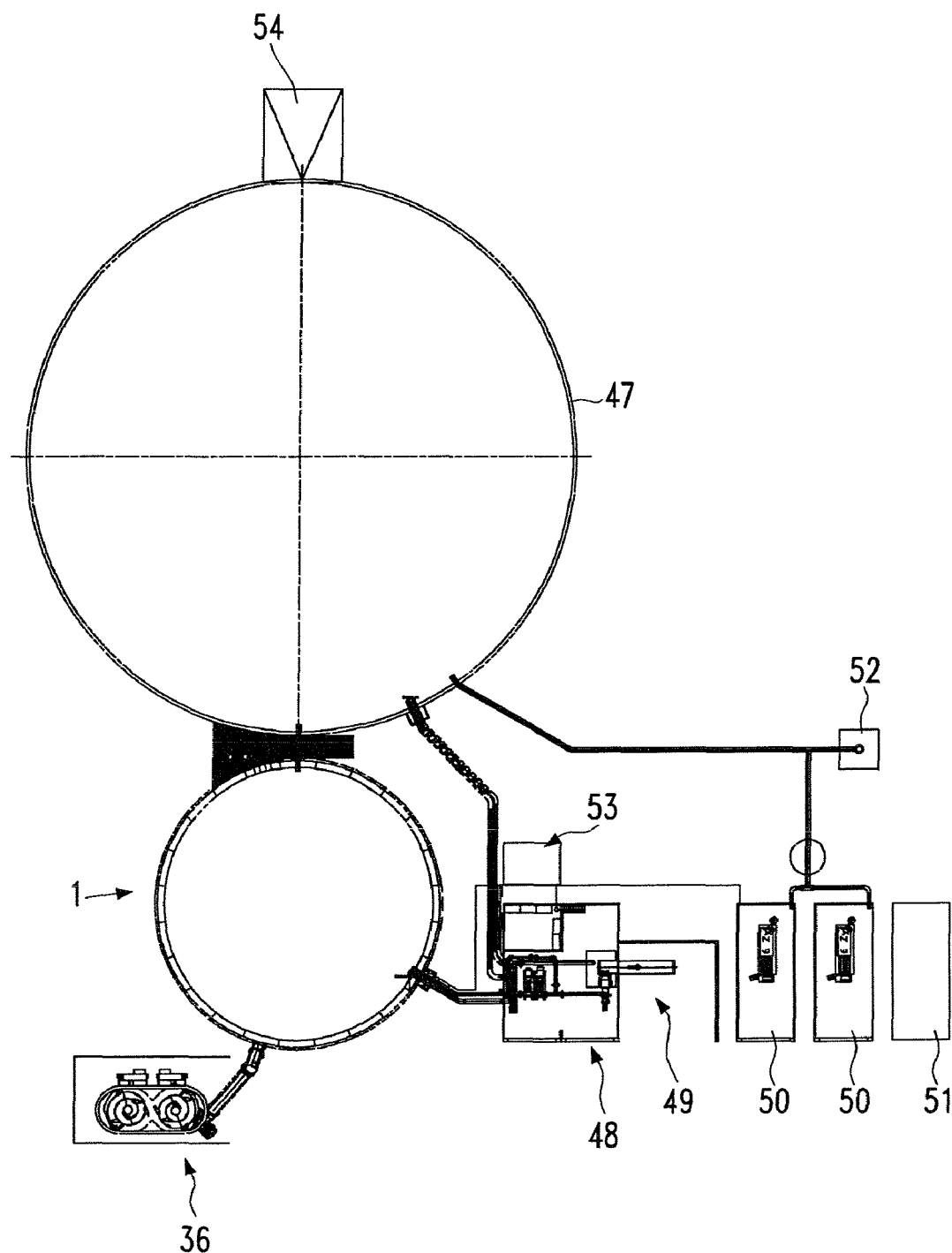
Figure 9:
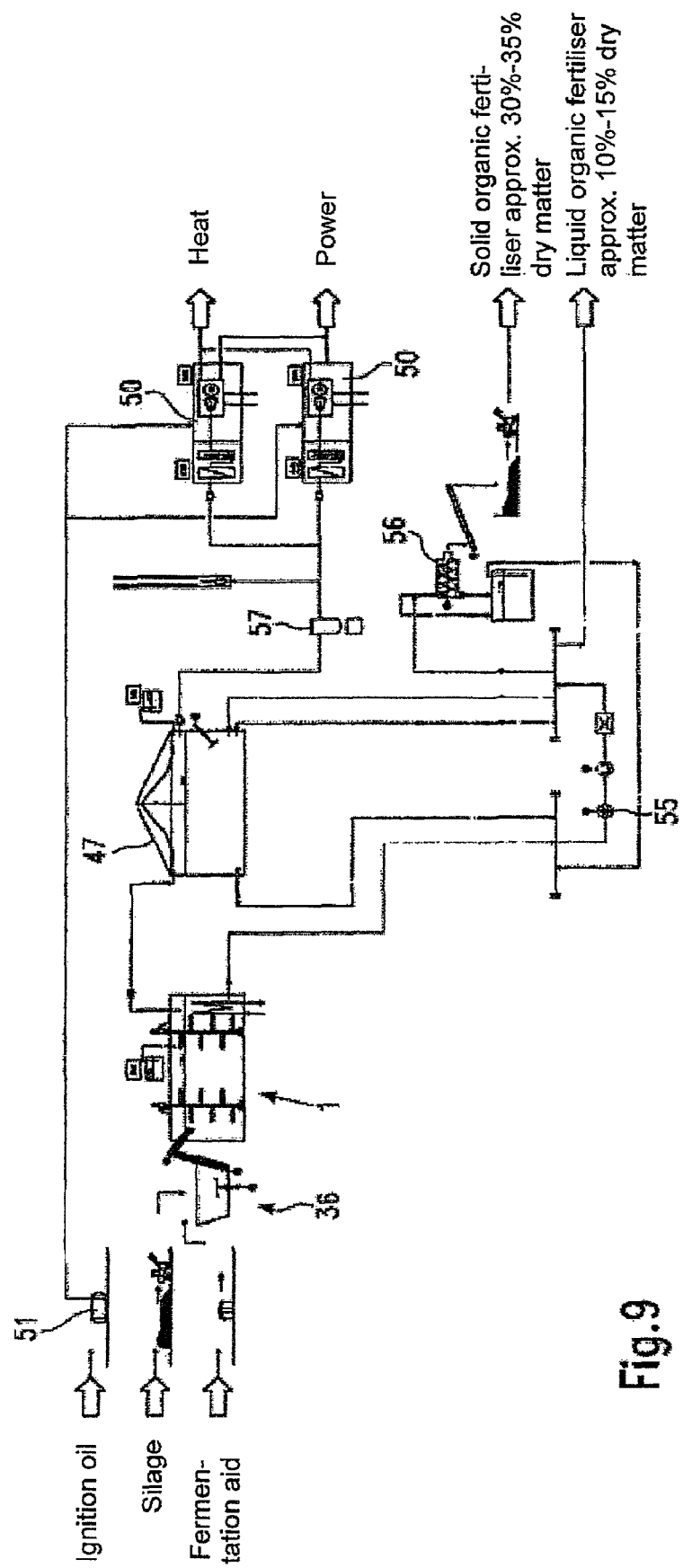
Figure 10:
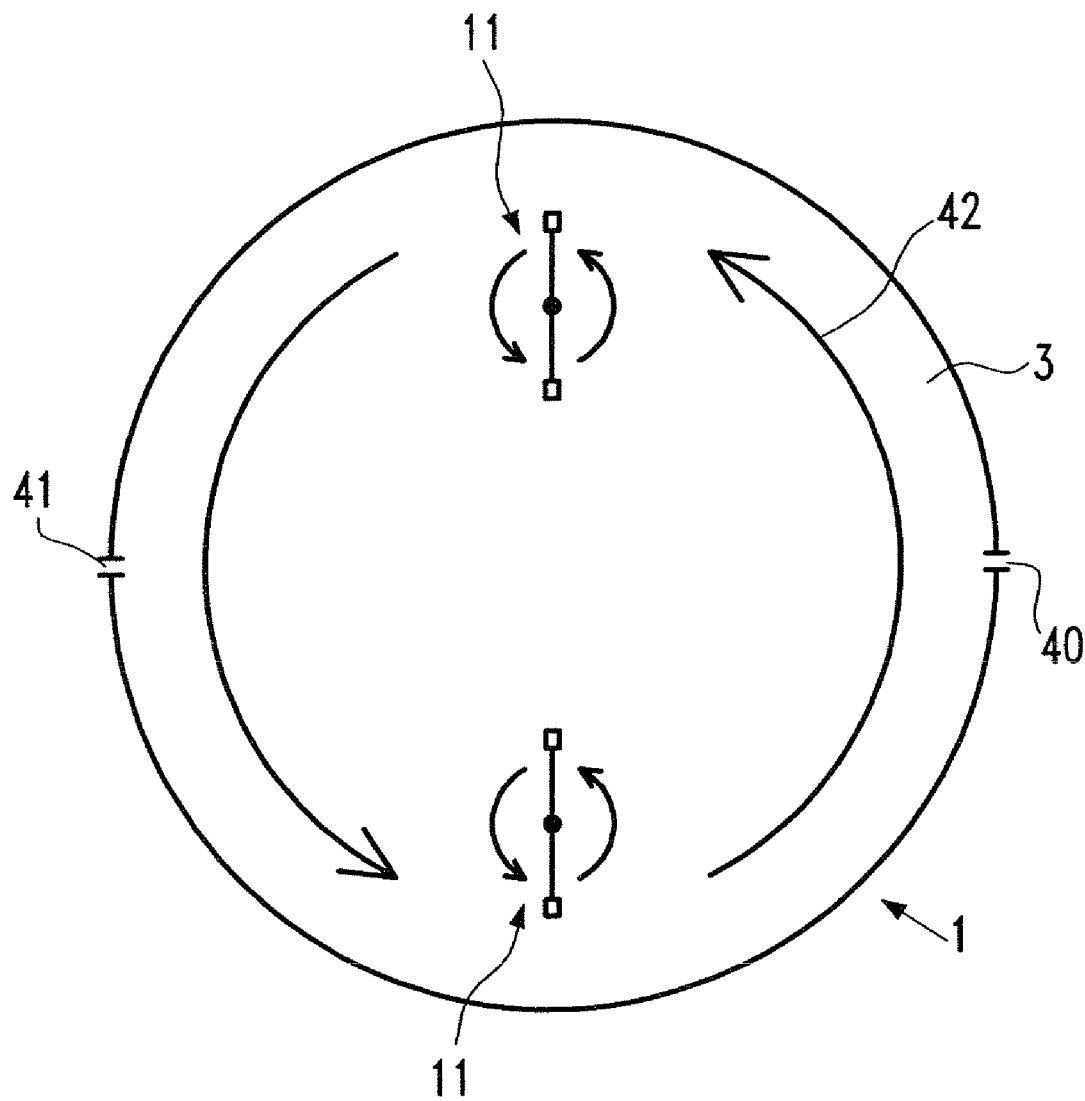

The invention is explained in detail and by way of example below with the aid of the drawings, which show schematically in:

FIG. 1 a fermenter according to the invention in a sectional view, together with the feeding device FIG. 2 a section through the fermenter of FIG. 1 in the area of an agitator FIG. 3 a partial section of the lower end section of an agitator FIG. 4 the centring bearing with an insertion funnel from FIGS. 1 to 3, viewed at an angle from above FIG. 5 insertion of an agitator into the fermenter in six steps FIG. 6 the fermenter body with a partly opened roof FIG. 7 a section through the fermenter body of FIG. 6 in a bottom corner area FIG. 8 the structure of a biogas plant with the fermenter according to the invention FIG. 9 a process flow chart of the processes operating in the biogas plant of FIG. 8, and FIG. 10 the flows in the fermenter of FIG. 1.

A fermenter 1 has a fermenter body 2 to hold a substrate 3 (FIG. 1).

The fermenter body 2 is formed of a base plate 4, circular when viewed from above, side walls 5 surrounding the base plate 4 and a roof 6 (FIGS. 6, 7). The side walls 5 and the roof 6 are made of precast concrete elements.

FIG. 7 shows a sectional view through a bottom corner area of the fermenter body with a circular base 7, the base plate 4 made of reinforced concrete and the side walls 5 made of reinforced concrete. The circular base 7 and the base plate 4 rest on a clean layer 8 made of macro-concrete. The individual precast concrete elements of the side walls 5 are braced together, with channels in the segments of the side walls 5 in which the tension flanges (not shown) run.

The roof too is made of several precast concrete elements, each forming individual circular segments. The roof sections rest with their broad ends on the side wall 5 and with their narrow ends on a support column 9 provided in the centre of the fermenter body 2. Some segments of the roof 6 are provided with an opening 10, the function of which will be explained in detail below.

The fermenter 1 has at least one agitator 11. The agitator 11 comprises:
an agitator shaft 12 which is roughly vertical,
a drive mechanism 13 acting on the upper end section of the agitator shaft 12 several agitator paddles 14, each fixed to the agitator shaft 12 by means of a paddle rod 15, and
a centring bearing 16 mounted on the base plate 4 to accommodate the lower end section of the agitator shaft 12.

The drive mechanism 13 is formed by an electric motor and a driving gear, and is mounted above the roof 6. The drive mechanism 13 is fixed to a cover plate 17 which covers the opening 10 of the roof 6. The agitator shaft 12 passes through the cover plate 17 with the aid of a conventional bearing. No additional sealing elements are needed since, in normal operation, the substrate does not come into contact with the roof 6 or the cover plate 17.

The agitator shaft 12 is formed by a steel tube which extends from the roof 6 to just above the surface of the base plate 4. The paddle rods 15 are clamped to the agitator shaft 12. This clamping may be effected at any desired point on the agitator shaft 12. It is thus possible to vary the number and the arrangement of the agitator paddles. The agitator paddles need not, as shown in FIGS. 1 and 2, be arranged on one plane. They may be offset relative to one another on the agitator shaft 12 at any desired angle.

The agitator paddles 14 and the paddle rods 15 each have flanges with corresponding holes (not shown), for fastening together by means of screw connections. By this means it is also possible to fasten the agitator paddles 14 to the paddle rods 15 at different angles of inclination from the vertical. In this way it is possible to vary the effective displacement surface of the agitator paddles 14 in the substrate 3 in the fermenter. The steeper the angle of the agitator paddles 14, the greater the effective displacement surface.

FIG. 3 shows a sectional view of the lower end section of the agitator shaft 12 which fits into the centring bearing 16. The centring bearing 16 has an insertion funnel 19 which leads into the centring section located below. Viewed from above, the centring section 20 is rectangular and is formed by four side walls. In principle the centring section may be of any shape which will provide non-rotatable engagement with a corresponding coupling element 28. In particular the shape of the centring section and the corresponding coupling element may be that of any other desired polyhedron. The centring section 20 is mounted at a distance h above a base plate 21. The centring section 20 and the insertion funnel 19 are held by supporting walls 22 which extend approximately radially outwards from the centring section 20. Since the centring section 20 is fitted at a distance h above the base plate 21, a free space and/or several openings are formed between the centring section 20 and the base plate 21, through which any substrate in the centring bearing 16 may be displaced when an agitator shaft 12 is inserted in the centring bearing 16.

Provided in the centre of the centring bearing 16 is a pedestal 23 in the form of a solid metal base. The pedestal is provided with a centring point 24 facing upwards.

Both the pedestal 23 and the centring bearing 16 are welded to the base plate 21 and are secured as a unit to the base plate 4 of the fermenter 1 at predetermined points. Since the centring bearing 16 is fixed immovably in the fermenter, the insertion funnel 19 may in principle be of any size desired. A large insertion funnel makes the insertion of the agitator in the fermenter considerably easier. The centring point 24 provides very precise alignment of the lower end section of the agitator shaft 12 in the fermenter.

The lower end of the agitator shaft 12 comprises a stub shaft 25 which is rotatably mounted in the tubular shaft body 26 of the agitator shaft 12. The stub shaft 25 is formed by a solid elongated rod 27 and a coupling element 28 provided on the lower end section of the rod 27. The coupling element 28 extends radially from the rod 27 and, viewed from above, has outer boundary surfaces of such a rectangular shape that they fit with minimal play into the centring section 20. Formed on the lower continuous edge of the coupling element 28 are lead-in bevels 29. The lower end face of the rod 27 has the shape of a conical recess which fits positively on to the centring point 24. The stub shaft 25 is thus centrally located by the centring bearing 16 and the pedestal 23, and the positive engagement between the centring section 20 and the coupling element 28 effects non-rotatable location of the stub shaft 25.

Provided in the tubular shaft body 26, a short distance above the upper end face of the stub shaft 25, is a circular disc-shaped stop 30. Between this stop 30 and this end face is a spherical roller bearing 31, through which the load of the agitator shaft 12 is transferred to the stub shaft 25, and which allows rotation of the shaft body 26 relative to the stub shaft 25.

In the area between the spherical roller bearing 31 and the coupling element 28, needle bearings 32 and plastic sleeves 33 encompassing the stub shaft 25 are arranged alternately. Provided on the inner surface of the shaft body 26 in the area below the stop 30 is a push-in tube 34 which serves on the one hand to insert the stub shaft 25 with the bearings 31, 32 into the lower end section of the shaft body 26, while on the other hand positioning the stub shaft 25 with the bearings 31, 32 and the plastic sleeves precisely in the shaft body 26.

Provided in the area between the coupling element 28, the push-in tube 34 and the bottom-most needle bearing 32 is a seal assembly 35 comprising several seal elements, which prevents the penetration of substrate into the space between the stub shaft 25 and the shaft body 26.

During operation of the fermenter, the agitator shaft 12 according to the invention may be withdrawn upwards, which involves the coupling element 28 siding out of the centring bearing 16. Only the centring bearing 16 and the pedestal 23 remain in the fermenter 1. These are heavy steel components which are not subject to any significant wear and do not require regular maintenance. The substantially more maintenance-intensive bearings 31, 32 are removed from the fermenter together with the agitator shaft 12 and may be serviced outside the fermenter, without any need to interrupt operation of the fermenter.

In the removal and insertion of the agitator shaft, the agitator paddles 14 and their associated paddle rods 15 are so aligned that they may be guided through the opening 10 in the roof 6 of the fermenter 1. Insertion of the agitator 11 into the fermenter 1 is shown schematically in FIG. 5.

In the present embodiment, the agitator paddles 14 and the paddle rods 15 each have an overall length of 1.4 m. The opening 10 preferably has a slightly greater width of e.g. 1.5 m, so that the strength of the roof 6 is not impaired, while at the same time the agitator 11 together with the agitator shaft 12 may be removed and reinserted. The complete replacement of an agitator shaft takes a few hours.

Provided for the feeding of input materials into the fermenter 1 is a feeding device 36 (FIG. 1) comprising a storage bin 37, a screw conveyor 38 and a conveyor channel 39. The conveyor channel leads into the upper part of the fermenter. It may lead into an opening in the roof 6, or in the upper edge area of the side wall 5. In the present embodiment the opening 40 is located in the upper edge area of the side wall 5. To remove the fermented material, a discharge outlet 41 is provided in the lower edge area of the side wall 5. Coupled to the discharge outlet is a pump (not shown), which conveys the fermented material on for further processing.

Since the feed inlet 40 is at the top of the fermenter and the discharge outlet 41 at the bottom, the fermenter is fed from top to bottom. Preferably the feed inlet 40 and the discharge outlet 41 are diametrically opposite in the fermenter so that, in flowing through the fermenter, the substrate must cross it completely once.

Operation of the fermenter 1 is described in detail below with the aid of the schematic representation of FIG. 10, which shows a plan view of the circular fermenter 1 with two agitators 11.

The input materials are fed in at the top of the fermenter 1 through the feed inlet 40. Suitable input materials for dry fermentation are substantially any recyclable stackable biomass with a dry weight content of at least 25%. These include e.g. silo maize, cereal whole plant silage, grass silage, sugar beet silage, fodder beet silage and cereals (rye, triticale, barley, wheat).

The two agitators 11 are operated in the same direction of rotation. The speed of rotation is low, with a maximum of 60 rpm. The typical speed of rotation in normal operation ranges from 0 to 20 rpm. It has been found that, with this arrangement of a vertically aligned agitator shaft and slow continuous rotation of the agitator shaft, the whole substrate 3 of the fermenter 1 is set in motion (see arrow 42). For this purpose it is advantageous if the fermenter is circular when viewed from above.

It has also been found that only a single agitator shaft is needed to move the whole of the substrate. For safety reasons, though, two or more agitator shafts are installed so that the substrate may be kept continuously in motion even if one agitator shaft fails. This avoids any rise in the liquid level in the fermenter through biogas inclusions in the scum layers.

With the continuous rotation and circulation of the substrate in the fermenter, three decomposition zones 43, 44 and 45 develop (FIG. 1). These three decomposition zones are layered one above the other. The uppermost zone is a liquefaction zone 43. The middle zone a methanation zone 44 and the bottom zone a discharge zone 45.

These three decomposition zones develop when the agitator paddles 14 are aligned substantially vertically, so that no appreciable movement up or down is generated in the substrate. Such vertically aligned agitator paddles 14 act on the substrate mainly on separate levels only, so that the levels are not mixed together. Preferably the uppermost paddles or the agitator paddles 14 located in the liquefaction zone 43 are set at a slight angle from the vertical, so that freshly added starting material is mixed immediately with the substrate of the liquefaction zone.

In another mode of operation, the agitator paddles are inclined relative to the vertical. With an angle of inclination of 20° to 70° and in particular of 30° to 60°, the substrate is mixed vertically to a considerable extent. If all the agitator paddles of an agitator shaft are inclined in the same direction, then a vertical flow of the substrate develops along the agitator shaft over the entire height which is filled with the substrate. Depending on the direction of the agitator shaft, the flow along the agitator shaft is directed upwards or downwards. In such a mode of operation, horizontal decomposition zones do not develop, but instead the whole substrate is mixed evenly.

The liquefaction zone contains the least decomposed substrate which, on account of its high organic content, has the lowest density. With progressive liquefaction the material sinks due to biological decomposition from the liquefaction zone into the methanation zone, where the majority of the methane is released. Due to its higher density, heavily decomposed substrate arrives at the discharge zone, from which it is removed through the discharge outlet 41.

The biogas evolved during this process collects below the roof 6 and is taken away through an opening 46 in the roof 6.

The level in the fermenter is monitored by means of a radar probe (not shown). If the filling level exceeds a certain height, the pump for discharge of the decomposed material switches on automatically.

The fermenter 1 is fed continuously by means of the feeding device 36. The storage bin 37 of the feeding device 36 may be filled by the operator in batches, with the control unit controlling the continuous feed by means of the screw conveyor 38. Through the discharge controlled by the radar probe, removal of the decomposed material is also continuous.

The typical mean hydraulic retention time of the substrate is around 40 days in the fermenter. The specific loading rate is 8 kg organic dry matter/m3/d.

Preferably the fermenter 1 is equipped with a heater which allows heating of the substrate in the fermenter, so that an optimal fermentation temperature in the fermenter may be maintained.

A biogas plant with the fermenter according to the invention is explained below. The biogas plant has a fermenter 1 with the feeding device 36, a combined after-fermenter/gas holder 47, a pump station 48, a storage facility for the solid fermentation products 49, two combined heat and power plants 50, an oil tank 51, a biogas emergency flare 52, a transformer station 53 and a filling point 54 for the liquid fermentation products.

In the storage bin 37 of the feeding device 36, silage is mixed with fermentation aids, and this mixture is fed as input material to the fermenter 1. The biogas produced in the fermenter is fed via the pump station 48 to the combined after-fermenter/gas holder 47. The fermented substrates are fed via the pump station 48 either to the after-fermenter/gas holder 47 directly or else via a disintegrator 55. The after-fermenter/gas holder 47 is a high-volume storage vessel with a double membrane, with the biogas to be found between the two membranes and below the lower membrane of the liquid fermentation product. The liquid fermentation product may be removed from the after-fermenter/gas holder 47 and/or the fermenter 1 and separated by a separator 56 from its solid constituents, which may be used as organic fertiliser, after which the separated liquid fermentation product is fed to the after-fermenter/gas holder 47. The dry substance content of the after-fermenter/gas holder 47 may thus be controlled by the separator 56. These fertilisers have a typical dry substance content of 30% to 35%.

The substrate decomposed in the fermenter 1 may also be used directly as organic fertiliser. This is a liquid fertiliser with a dry substance content of 10% to 15%.

The biogas stored in the after-fermenter/gas holder 47 is fed via a condensate trap 57 to the combined heat and power plants 50 to generate power and heat. The oil tank 51 is provided to supply the combined heat and power plants 50 with ignition oil. Biogas may also be burned by an emergency flare 52 when the combined heat and power plants are unable to process the amount of biogas supplied.

The invention may be summarised briefly as follows:

The invention relates to an agitator for a fermenter, a fermenter and method of operating a fermenter.

The agitator shaft has an agitator shaft which according to the invention stands approximately upright in the fermenter. By this means the substrate in the fermenter is circulated in horizontal planes. This allows the formation of several layered decomposition zones.

The agitator is also preferably so designed that it may be removed upwards from the fermenter during continuing operation. Because of this, it is not necessary to empty the fermenter to carry out maintenance work on the agitator.

LIST OF REFERENCE NUMBERS

1 fermenter
2 fermenter body
3 substrate
4 base plate
5 side wall
6 roof
7 circular base
8 clean layer
9 support column
10 opening
11 agitator
12 agitator shaft
13 drive mechanism
14 agitator paddle
15 paddle rod
16 centring bearing
17 cover plate
18
19 insertion funnel
20 centring section
21 base plate
22 supporting walls
23 pedestal
24 centring point
25 stub shaft
26 shaft body
27 rod
28 coupling element
29 lead-in bevel
30 stop
31 spherical roller bearing
32 needle bearing
33 plastic sleeve
34 push-in tube
35 seal assembly
36 feeding device
37 storage bin
38 screw conveyor
39 conveyor channel
40 feed inlet
41 discharge outlet
42 arrow
43 liquefaction zone
44 methanation zone
45 discharge zone
46 opening
47 after-fermenter/gas holder
48 pump station
49 storage facility
50 combined heat and power plant
51 oil tank
52 biogas emergency flare
53 transformer station 54 filling point
55 disintegrator
56 separator
57 condensate trap

The invention claimed is:

1. An agitator for a fermenter, comprising
at least one vertical agitator shaft, to which is fitted at least one agitator paddle,
a drive mechanism which rotates the agitator shaft, the drive mechanism driving an upper end section of the agitator shaft, and
a centering bearing for centering the lower end of the agitator shaft, wherein the centering bearing is designed to be releasable from the agitator shaft in such a way that the agitator shaft may be centered by pushing into the centering bearing and held in the centering bearing solely by the force of gravity on the agitator shaft, wherein the centering bearing has an insertion funnel and includes a centering section disposed below the insertion funnel, wherein the agitator shaft includes a stub shaft at its lower end section, the stub shaft rotatably mounted with a bearing so as to be rotatable relative to a rest of the agitator shaft, and wherein the stub shaft includes a coupling element which positively engages the centering section.

2. The agitator of claim 1, wherein the agitator paddles are set at different angles relative to the vertical.

3. The agitator of claim 1, wherein the centering bearing has a centering section which, viewed from above, has the shape of a polyhedron.

4. The agitator of claim 3, wherein the polyhedron is a square.

5. The agitator of claim 4, wherein the centering bearing has in its lower part an opening through which material may be displaced on insertion of the agitator shaft into the centering bearing.

6. The agitator of claim 1, wherein the centering bearing has in its lower part an opening through which material may be displaced on insertion of the agitator shaft into the centering bearing.

7. The agitator of claim 1, wherein a pedestal is provided within the centering bearing.

8. The agitator of claim 7, wherein the pedestal includes a centering point directed upwards.

9. The agitator of claim 1, wherein the agitator shaft comprises a tubular shaft body in which the stub shaft is mounted, with the stub shaft projecting a short distance from the shaft body.

10. The agitator of claim 9, further comprising a component selected from the group consisting of a ball, roller, needle bearing, and combinations thereof, wherein the component is arranged between the stub shaft and the shaft body.

11. The agitator of claim 1, wherein the centering section is disposed below the insertion funnel in a direction of pushing the agitator shaft into the centering bearing, and is stationary relative to the insertion funnel.

12. The agitator of claim 1, wherein the centering section is disposed below the insertion funnel such that the insertion funnel overlays and feeds into the centering section, and is stationary relative to the insertion funnel.

13. A fermenter comprising:
a housing comprising at least one base plate and one or more side walls surrounding the base plate,
the agitator of claim 1,
a feeding device for feeding input materials, and
a discharge outlet,
wherein the feeding device is provided in the upper section of the fermenter, and the discharge outlet is provided in the lower section of the fermenter.

14. The fermenter of claim 13, wherein the discharge outlet of the fermenter is arranged diametrically opposite the feeding device.

15. The fermenter of claim 14, wherein the side wall, viewed from above, is circular in shape.

16. The fermenter of claim 15, wherein the housing further comprises a roof.

17. A method of operating a fermenter, comprising:
providing the fermenter to include:
a housing including a roof with an opening provided in the roof;
a feeding device for feeding input materials;
a discharge outlet, wherein the feeding device for the feeding in of input materials is situated in the upper section of the fermenter, and the discharge outlet is situated in the lower section of the fermenter; and
an agitator, the agitator comprising:
at least one vertical agitator shaft, to which is fitted at least one agitator paddle extending horizontally from the agitator shaft;
a drive mechanism which rotates the agitator shaft, the drive mechanism driving an upper end section of the agitator shaft; and
a centering bearing for centering the lower end of the agitator shaft, wherein the centering bearing is designed to be releasable from the agitator shaft in such a way that the agitator shaft may be centered by pushing into the centering bearing and held in the centering bearing solely by the force of gravity of the agitator shaft, wherein the centering bearing has an insertion funnel and is provided with a centering section disposed below the insertion funnel, and at the lower end section of the agitator shaft there is provided a stub shaft, mounted by means of a bearing so as to be rotatable relative to a rest of the agitator shaft, and the stub shaft has a coupling element which positively engages the centering section, and
inserting and removing the agitator from the housing by rotating the agitator shaft such that the agitator paddles are individually aligned relative to the opening so that the agitator shaft may be inserted and removed through the opening provided in the roof, the opening provided in the roof being slightly larger than a length of individual agitator paddles.

* * * * *